United States Patent
Wagner

(10) Patent No.: US 7,576,849 B2
(45) Date of Patent: Aug. 18, 2009

(54) METHOD AND APPARATUS FOR OPTICALLY CONTROLLING THE QUALITY OF OBJECTS HAVING A CIRCULAR EDGE

(75) Inventor: Robert Wagner, Neuburg am Inn (DE)

(73) Assignee: Micro-Epsilon Messtechnik GmbH & Co. KG, Ortenburg (DE)

( * ) Notice: Subject to any disclaimer, the term of this patent is extended or adjusted under 35 U.S.C. 154(b) by 0 days.

(21) Appl. No.: 11/280,022

(22) Filed: Nov. 16, 2005

(65) Prior Publication Data

US 2006/0072105 A1    Apr. 6, 2006

Related U.S. Application Data

(63) Continuation of application No. PCT/DE2004/000474, filed on Mar. 10, 2004.

(30) Foreign Application Priority Data

| May 19, 2003 | (DE) | ................................ | 103 37 727 |
| Oct. 9, 2003 | (DE) | ................................ | 103 47 625 |
| Nov. 11, 2003 | (DE) | ................................ | 103 52 936 |

(51) Int. Cl.
    *G01N 21/00*    (2006.01)
(52) U.S. Cl. .................................................. 356/237.1
(58) Field of Classification Search ... 356/237.1–237.5, 356/394, 614; 250/559.29, 559.36, 559.46, 250/559.42; 348/126, 128
    See application file for complete search history.

(56) References Cited

U.S. PATENT DOCUMENTS

| 4,328,553 | A | * | 5/1982 | Fredriksen et al. ..... | 356/139.04 |
| 6,038,029 | A | | 3/2000 | Finarov | |
| 6,147,357 | A | * | 11/2000 | Nicolesco ............... | 250/559.46 |
| 6,249,342 | B1 | * | 6/2001 | Cheng ..................... | 356/237.2 |
| 6,297,879 | B1 | * | 10/2001 | Yang et al. ............... | 356/237.5 |
| 6,324,298 | B1 | * | 11/2001 | O'Dell et al. ............. | 382/149 |
| 6,489,626 | B2 | | 12/2002 | Van der Muehlen et al. | |
| 6,501,546 | B1 | * | 12/2002 | Weiss ....................... | 356/239.1 |
| 6,541,747 | B1 | * | 4/2003 | Kikuchi et al. ........... | 250/201.2 |
| 6,545,752 | B1 | | 4/2003 | Swan et al. | |
| 6,906,794 | B2 | * | 6/2005 | Tsuji ........................ | 356/237.4 |
| 6,947,588 | B2 | * | 9/2005 | Sim .......................... | 382/149 |
| 7,079,237 | B2 | * | 7/2006 | Woo et al. ................ | 356/237.2 |
| 7,102,743 | B2 | * | 9/2006 | Tsuji et al. ............... | 356/237.2 |
| 7,149,341 | B2 | * | 12/2006 | Hayashi et al. ........... | 382/145 |
| 2002/0001403 | A1 | * | 1/2002 | Kikuchi .................... | 382/145 |
| 2002/0131166 | A1 | * | 9/2002 | Woo et al. ................ | 359/391 |
| 2002/0168787 | A1 | | 11/2002 | Noguchi et al. | |

(Continued)

FOREIGN PATENT DOCUMENTS

DE    101 31 665 A1    1/2003

(Continued)

*Primary Examiner*—Hoa Q Pham
(74) *Attorney, Agent, or Firm*—Alston & Bird LLP

(57) ABSTRACT

Method and apparatus for optically testing the quality of objects such as silicon wafers which have a circular peripheral edge, wherein light is directed onto the edge region of the object, and the light radiating from the object due to reflection, refraction and/or diffraction is detected by means of a measuring unit which produces an image from the received light. Defects on and/or in the object are identified from the produced image.

28 Claims, 2 Drawing Sheets

U.S. PATENT DOCUMENTS

| | | |
|---|---|---|
| 2003/0053046 A1 | 3/2003 | Ise et al. |
| 2003/0202178 A1* | 10/2003 | Tsuji et al. ............... 356/237.2 |
| 2005/0036671 A1* | 2/2005 | Watkins et al. .............. 382/145 |

FOREIGN PATENT DOCUMENTS

| | | | |
|---|---|---|---|
| EP | 0 100 446 A1 | | 2/1984 |
| EP | 0 499 312 A1 | | 8/1992 |
| EP | 0 766 298 A2 | | 4/1997 |
| EP | 1 001 460 A1 | | 5/2000 |
| JP | 406258231 A | * | 9/1994 |
| JP | 2000 046743 A | | 2/2000 |
| JP | 200046537 A | * | 2/2000 |
| WO | WO 98/59235 A1 | | 12/1998 |
| WO | WO 99/67626 A1 | | 12/1999 |
| WO | WO 02/35217 A2 | | 5/2002 |

* cited by examiner

METHOD AND APPARATUS FOR OPTICALLY CONTROLLING THE QUALITY OF OBJECTS HAVING A CIRCULAR EDGE

CROSS REFERENCE TO RELATED APPLICATION

The present application is a continuation of international application PCT/DE2004/000474, filed 10 Mar., 2004, and which designates the U.S. The disclosure of the referenced application is incorporated herein by reference.

BACKGROUND OF THE INVENTION

The invention relates to a method for optically testing the quality of objects which normally have a circular edge, wherein light is directed to the edge of the object. Furthermore, the invention relates to an apparatus for optically testing the quality of such objects, in particular for carrying out the method of the invention, with at least one light-emitting illumination unit for illuminating the edge of each object.

Methods and apparatus of the type under discussion have been known from practical operation for a long time, and they play a more and more important role within the scope of a complete inspection of objects, in particular products of industrial production. These methods and apparatus concern not only a most complete possible inspection of the finished product prior to delivery or a comprehensive acceptance test. Rather, there also exists a developing trend to repeatedly ensure the quality of the intermediate product already between individual manufacturing steps, and to thus enable an early detection of product imperfections or also manufacturing errors.

In the field of the semiconductor industry, a plurality of inspection systems have thus become established over the years, which detect a great variety of criteria in the production of silicon wafers. The efficiency of these systems represents the basis for establishing international standards (SEMI standards, Semiconductor Equipment and Materials International) for the quality of the product "wafer," so as to make available a worldwide uniform definition for all enterprises operating in the semiconductor industry.

A very critical feature for the quality of wafers is the condition of the wafer surface, where it matters that individual particles, contamination, roughness, and defects be detected with a very high resolution. On their part, the wafer manufacturers intend to perform not only a quality inspection at the end of each production line within the scope of a final inspection, but to provide also such an inspection in several points of the manufacturing process, and to ensure that faulty silicon slices are sorted out at an earliest possible time as a function of the type or the distribution of imperfections, for purposes of thus preventing further processing in the production which is connected with high costs, or even a delivery of such slices to customers.

Visually detectable defects, even when these are not obvious and visible only with special illumination and with the aid of magnifying optical systems, lead at the customers' end largely to the following problems:

1. Early detection of defects (for example, within the scope of the acceptance test) normally leads to a complaint and return of the delivered wafer. A consequence resulting therefrom is, for example, the delay in further processing and, thus, a corresponding outage of production times.

2. If defects are detected only in the further manufacturing process or at the end of further processing, it will become necessary to separate a costly manufactured and thus a higher valued product as a whole. This unnecessarily reduces the actual production capacity on the one hand, while on the other hand, costs for the rejected product have already been incurred within the scope of further processing.

3. If an undetected defect even leads to a break of the wafer in the course of further processing, one will have to add to the mere material costs, which in this case already amount per se to considerable sums, the costly restoration of clean-room conditions after such an occurrence and the therewith connected shutdown of an entire production line.

In the current state of the art, the automated inspection of the wafer surface with respect to particles, roughness, and defects excludes the edge zone of the wafer from the inspection. This edge zone is defined by the SEMI standards as the transitional region from the front side of the wafer to the backside thereof, and moreover respectively a range of three millimeters starting from the edge region into the surface of the wafer.

Since the edge region of the wafer (=edge+part of the edge zone, in particular the exclusion zones as are defined by current SEMI standards in the inspection of surfaces) is at the present totally excluded from the definition of quality standards for wafer surfaces, the edge region of the wafer is currently subjected only to a manual, visual inspection by an operator. In this inspection, very strong light sources are used as auxiliary devices to be able to detect possible defects on the edge of the wafer. In this process, one examines in particular the edge for light reflections, which are caused by unevennesses. However, from the viewpoint of manufacture and further processing, the reliability and reproducibility of this visual method are the worst conceivable, which has until now prevented defining quality standards in an analogous manner to the front and the backside.

Besides the visual, scattered-light inspection by an operator, which must be considered inherently subject to errors, there currently exists only one automated device for inspecting wafers, namely the "edge scan" device from Raytex, which examines the edge of the wafer, but not the edge zone. This system that is based on a scattered-light evaluation of the laser beam which is perpendicularly directed to the edge, but this system inadequately meets customer demands. On the one hand, this is due to a too low resolution of the system (one measured value for 25 µm of the wafer circumference) and the resultant limited sensitivity. Furthermore, the scattered-light evaluation as used is sensitive to deviations of the wafer from its ideal geometry (warping), the profile of the edge that is to be made, and the handling of the wafer during the measurement itself (tilting of the wafer relative to the axis of the laser beam).

A classification of defects by their more specific type (contamination, scratches, chipping, coating, particles, etc.) within the scope of the visual inspection has until now been possible only in a further, time-consuming step by examining the damaged wafer in greater detail under a microscope. For the available automated system, an assessment of detected imperfections is likewise ensured only by an operator, who must analyze to this end a camera picture of each defect. With that, more extensive, statistic tests and detection of systematic errors have until now likewise not been possible or realized.

As a whole, the edge of a wafer becomes more and more important, which results from the edge handling of wafers with a diameter of 300 mm as is recommended by the SEMI standard. This region is thus exposed to additional, mechanical stresses, which in part only cause defects that are to be detected, or which sensitively react to existing defects.

Since the demand for larger wafer diameters steadily increases, and quality requirements become greater to the same extent, there exists, in particular on the part of the wafer producers, a need for a fully automated system for inspecting the wafer edges with respect to defects and roughness, namely a system which is in a position to measure silicon slices accurately, to standards, in a manner free of contamination and destruction in and between the corresponding production steps of the wafer manufacture, and to detect and classify imperfections.

It is therefore an object of the present invention to improve and further develop a method and an apparatus of the initially described type for optically testing the quality of objects with a circular edge in such a manner that they permit a reliable, reproducible inspection of the object edge with great accuracy.

SUMMARY OF THE INVENTION

In accordance with the invention, the foregoing object is accomplished by a method for optically testing the quality of objects with a peripheral edge region, wherein light is directed onto the edge region of the object, and wherein light radiating from the object due to reflection, refraction and/or diffraction is detected by means of a measuring unit. The detected light is processed in the measuring unit to produce an image, and the produced image is evaluated to permit an identification of defects on and/or in the object.

It has been found to begin with that increasingly greater importance is attached to the testing of the edge region of objects with a circular edge. Moreover, it has been found that the currently, merely visual inspection of the edge region for quality by an operator is highly susceptible to errors and barely reproducible. In accordance with the invention, the measuring unit is used to detect the light that radiates from the object by reflection, refraction and/or diffraction. Finally, it has also been found by the invention that defects on and/or in the object can be detected by means of the detected image signals in a reliable and reproducible manner and with great accuracy.

The method of the invention can be applied to a plurality of inspection tasks within the scope of a surface check. The object could in principle be any type of object, preferably however, workpieces or finished products from industrial production, such as, for example, rod and pipes, stampings, rolling stock, etc. The object could be at least partially transparent, i.e., the object could be, for example, a lens. However, as aforesaid, a primary field of application is the quality testing of semiconductor slices, in particular silicon wafers. For this reason, reference is made in the following exclusively to wafer slices.

Besides an automated optical detection of defects in the edge region of wafers, it would be possible to perform in an advantageous manner an automated classification of the found defects.

By combining image processing components, such as cameras, lenses, or illumination modules, and efficient image processing algorithms, the edge inspection system detects defects and particles in the image data of the wafer edge, which are supplied by the cameras. The found deficiencies could subsequently be automatically classified with the use of image processing software either by means of form or intensity features over parameterizable ranges, or on the basis of a catalog of defects. The catalog of defects could be prepared on the basis of image data earlier obtained from preceding measurements. In addition, the automatic classification of the found defects could be trained as a self-learning system on the basis of a number of images of sample defects of one class. Subsequently, it would be possible to perform an automatic classification with neuronal networks.

The edge inspection system "films" the wafer edge while rotating the wafer, and analyzes the received image signals with respect to defects by means of image processing software. Criteria for the detection of defects are primarily changes in form, i.e., geometric features, as well as deviations of the reflected light intensity, which can become noticeable, for example, as brightness differences in the recorded image data. The detected defects are ultimately subjected to a classification, which is performed in accordance with the measuring result by comparison with a collection of exemplary defects. To this end, it would be possible to use a neuronal network with monitored training. As a more extensive processing, it is possible to sort the wafers on the basis of the classification result into individual classes representing, for example, different degrees of quality.

For a simultaneous and real time capable image acquisition and image evaluation, optimized image processing software modules are provided, which enable online with the supplied data, a reliable and repeatable detection of defects. Besides this online evaluation during the measuring step, it is likewise possible to detect the defects from the image data in a processing step subsequent to the measurement, i.e., an offline evaluation of the raw data.

As aforesaid, it is possible to use as basis of the defect classification a catalog of defects with a division into classes, which is composed of exemplary defects for each class that were earlier detected with the aid of the measuring system, and which can be enlarged at any time with additional classes or modified within the class by adding and deleting individual examples.

In an advantageous manner, it would be possible to monitor the distance between the wafer and the measuring unit automatically. A corresponding tracking of the relative position between the measuring unit and the wafer would be able to prevent effectively impairments of the image quality, which result from distance variations occurring during the measurement. To compensate tolerances of such a tracking system and the wafer geometry, it would be possible to integrate an intelligent controlling and regulating interface, which responds within very short reaction times to changes of the actual relative position between the test object and the measuring unit, and which keeps the distance as constant as possible during the measurement via a corresponding regulating process. In this connection, it is possible to track both the measuring unit with respect to the stationarily held wafer and the wafer with respect to the stationarily held measuring unit, namely both for all axes and selectively for individual axes.

An automatic detection of defects in the edge region of the wafer could be performed, for example, effective a defect size smaller than 1 μm, with a finer resolution being basically possible. To this end, the measuring unit could provide a measured value for every 2 μm of the circumference of the wafer and 2 μm in the direction of the edge region. In comparison with the system of the art, this would mean a more than 1000 times increase in the resolution and in addition a complete coverage of the edge region.

As regards the apparatus, the initially described object is accomplished by at least one light emitting illumination unit for illuminating the edge of the object, and a measuring unit comprising an optical imaging system which is capable to imaging light radiating from the object due to reflection, refraction, and/or diffraction, and an evaluation unit. This permits determining defects on and/or in the object by means of the produced image signals. Preferably, the apparatus of the invention is used to carry out the method as described above, so that the foregoing part of the specification is herewith incorporated by reference for purposes of avoiding repetitions.

Concretely, it would be possible to use as the illumination unit LEDs, cold-light sources, in particular controllable high-output cold-light sources, lasers, or conventional light sources. In an advantageous manner, the luminous flux density of the illumination unit could be adapted for variable adjustment, so that it is possible to adjust, for example, a low light intensity for testing rough surfaces, and a higher light intensity for polished surfaces. In particular, it would be possible to choose the luminous flux density such that a high sensitivity results for small defects or a low sensitivity for detailed structures of large or superposed defects. In addition or as an alternative, the angle of illumination could also be variable, for example, by pivoting the illumination unit.

In an advantageous manner, the measuring unit could comprise a camera system consisting of a plurality of cameras. In this instance, it would be possible to use both matrix-array cameras and linear-array cameras. Concretely, the cameras could be arranged, for example, in a semicircle in symmetric relationship with the wafer. In particular, the cameras could be pivotally arranged, so that it would be possible to take pictures of the object from different angles of view.

To be able to examine the complete edge of a wafer while gripping its edge, two sequential measurements are needed. Between the two measurements, the wafer is gripped again in a different location, so that it is possible to inspect in the second measurement regions that were covered by the handling during the first measurement. With a measuring time of less than 15-20 seconds for every 300 mm of wafer—without regripping, i.e., regions that are possibly covered by the handling of the wafer are treated as exclusion zone—or a measuring time of less than 30-40 seconds per wafer—including regripping and measurement of the regions that were covered by the handling during the first rotation of the wafer—while excluding each time the robot handling for supplying the wafer, the throughput of the system is oriented toward the practical use in the production, which handles 60 or more wafers per hour. It follows from these requirements as to the throughput that the exposure time for taking one scanning line is in a range of a few microseconds, and that thus special requirements must be met as to the sensitivity of the linear-array cameras in use, the light intensity of the optical imaging system, and the intensity of the sources of illumination. For such short integration times, the use of highly sensitive time delay integration (TDI) sensors has been found advantageous on the part of the linear-array cameras. Unlike conventional linear-array cameras, same use a plurality of parallel arranged individual components, which take with a time delay one and the same linear section of the object being covered. By a subsequent integration of the respective individual signals, the camera provides a clearly improved image signal, and with that a higher sensitivity is achieved altogether.

For taking the images, it is furthermore possible to use special optical magnifying systems, which distinguish themselves by high resolution, maximum depth of definition, and at the same time by high light transmission to be able to achieve the desired detection sensitivity.

As illumination, it would be possible to use for each camera a radially symmetric dark-field illumination, which permits detecting defects irrespective of their orientation. In the case of the dark-field illumination, the light incidence could be made variable, so that it would be possible to perform a plurality of measurements on the object for purposes of greater information density, for example, a first measurement with a light incidence of 20°, and a subsequent measurement with a light incidence of 45°. As an alternative to sequential measurements with changed adjustments, luminous flux density, angle of illumination, angle of view of the camera, etc., by means of a single system, it is likewise possible to integrate a plurality of systems with respectively different arrangements, which permit performing the measurements parallel with changed adjustments for purposes of not reducing the throughput during the quality inspection.

Yet, the basically, i.e., theoretically achievable depth of definition of such an optical system is upwardly limited. For this reason, one uses in addition a means for tracking the camera and illumination system to maintain a constant distance from the edge of the wafer, so as to be able compensate acceptable geometry deviations of the wafer itself and deflections during the rotation of the wafer by the handling system.

Since comparability of the measurements between systems of identical construction matters greatly in the production, it would be possible to use mechanisms to integrate the mutual adaptation of different systems in the sense of a calibration.

Long-term fluctuations of measuring results because of aging processes of individual components, for example, in the form of variations of light intensity of the sources of illumination, as well as because of environmental influences, for example, temperature influences, could be compensated on the measuring unit by integrated methods on the basis of regularly performed check measurements and statistic evaluations of these results with respect to a long-term stabilization of the measuring system.

Both for the calibration and for the long-term stabilization, it is provided to use not only objects—reference pieces—that have been measured several times and taken from the regular production, but also test objects—master pieces—that have been specially made and defined for these tasks.

Since measuring principles which are currently applied to inspect the quality of smooth surfaces, in particular wafer surfaces (structured light and scattered-light evaluation), are not transferable to curved surfaces, even with clearly reduced requirements, in comparison with the accuracy in the nanometer range as is usual in the examination of wafer surfaces, the optical inspection with image processing methods represents an alternative approach. Moreover, this approach also offers as an integrated component of the system, the possibility of a trainable classification that is comparable with a visual classification.

In the years to come, the edge zone of the wafer will represent an increasingly more decisive quality criterion for silicon slices as a result of the foreseeable increased use of the edge handling as is recommended within the SEMI standards. For the production of wafers in the 300 mm range that can be processed on both sides, the until now largely applied vacuum handling on the backside will be eliminated, since such a contact of the wafer is always accompanied by contaminations on the surface. This technology, therefore, leaves only the possibility of effecting production and further processing of wafers by means of edge gripping and edge handling.

Likewise, in the field of the wafer-processing industry, the need for automated inspection systems for the wafer edge will increase in new production lines as a result of the increasing mechanical stress on the wafer edge by means of the edge handling. In the case of a successful use of the method (starting with applications within the scope of acceptance tests), one can also expect in this sector a multiple use within the particular production lines.

There exist various possibilities of improving and further developing the teaching of the present invention in an advantageous manner. To this end, one may refer to the following description of a preferred embodiment of the invention with reference to the drawings. In conjunction with the description of the preferred embodiment of the invention with reference to the drawings, also generally preferred improvements and further developments of the teaching are described.

DETAILED DESCRIPTION OF THE PREFERRED EMBODIMENT

Figure 1:
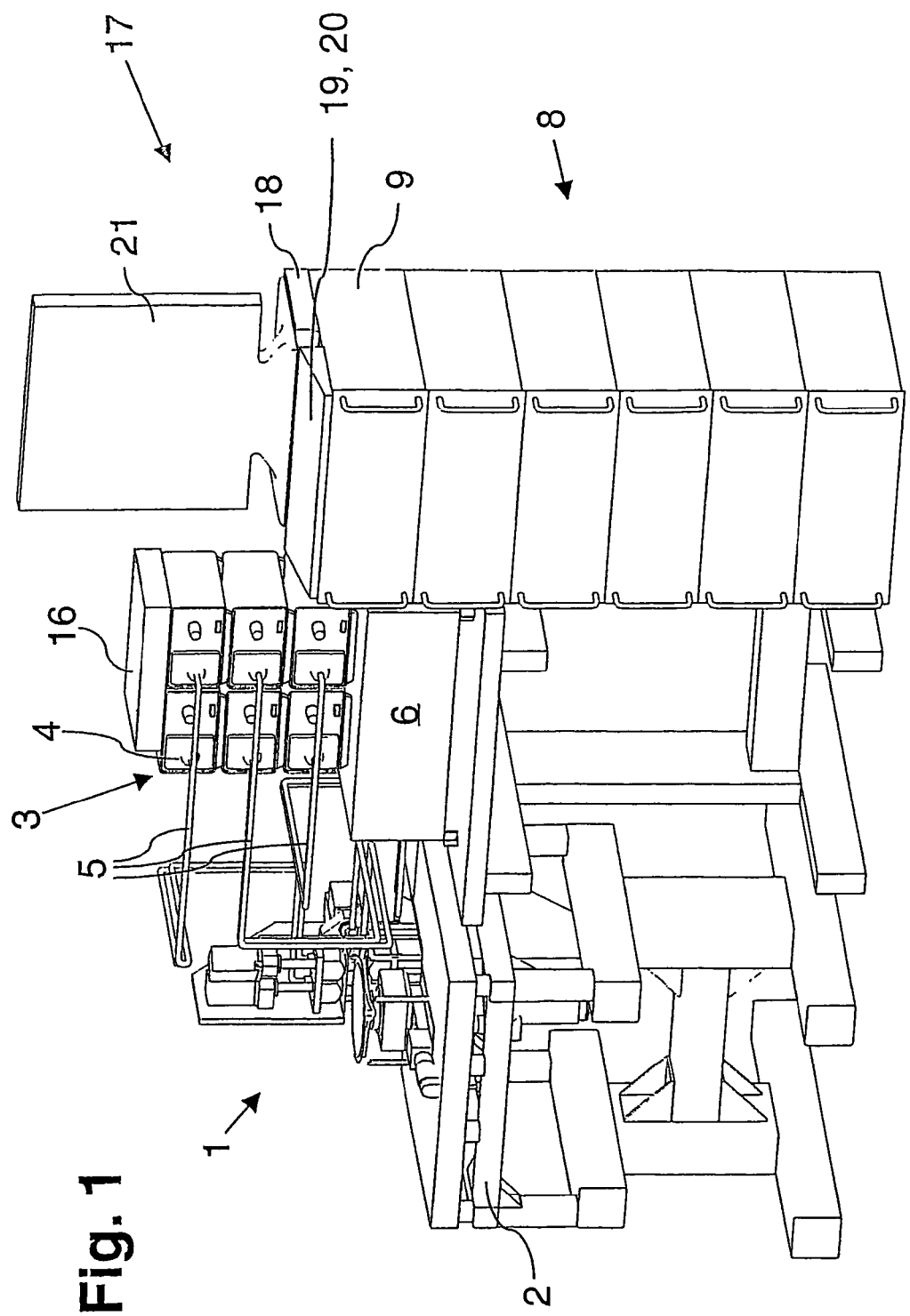
FIG. 1 is a perspective view of an embodiment of the apparatus according to the invention for optically testing the quality of objects having a peripheral edge region, in particular wafer slices made of silicon.

Referring more particularly to the drawings, the apparatus of the invention comprises a measuring unit 1, which is described in greater detail below, and which is arranged on a base 2 that is supported as much as possible in a vibration free manner. Besides the base 2, an illumination unit 3 is provided, which comprises a total of six high-output cold-light sources 4. To each light source 4, a light guide 5 is associated, which supplies the light of the light sources 4 to the measuring unit 1. Below the illumination unit 4, an amplifier unit 6 is provided for a motor-operated activation to readjust the properties of optical imaging systems 7 of the measuring unit 1 (see FIG. 2) in the sense of a vario-focus.

An evaluation unit 8 is also provided which comprises a total of six industrial evaluation PCs 9. The PCs 9 are associated to a total of six camera systems 10, 11, 12, 13, 14, 15 such that respectively one PC 9 processes the measured data of one camera system 10-15. A hub 16 serves for communication between the evaluation computers 9 which connect to the hub 16 via a network interconnection.

A uniform, central operator interface is provided by means of a single work station 17 with the aid of switches 18 for a mouse 19, keyboard 20, and screen 21.

Figure 2:
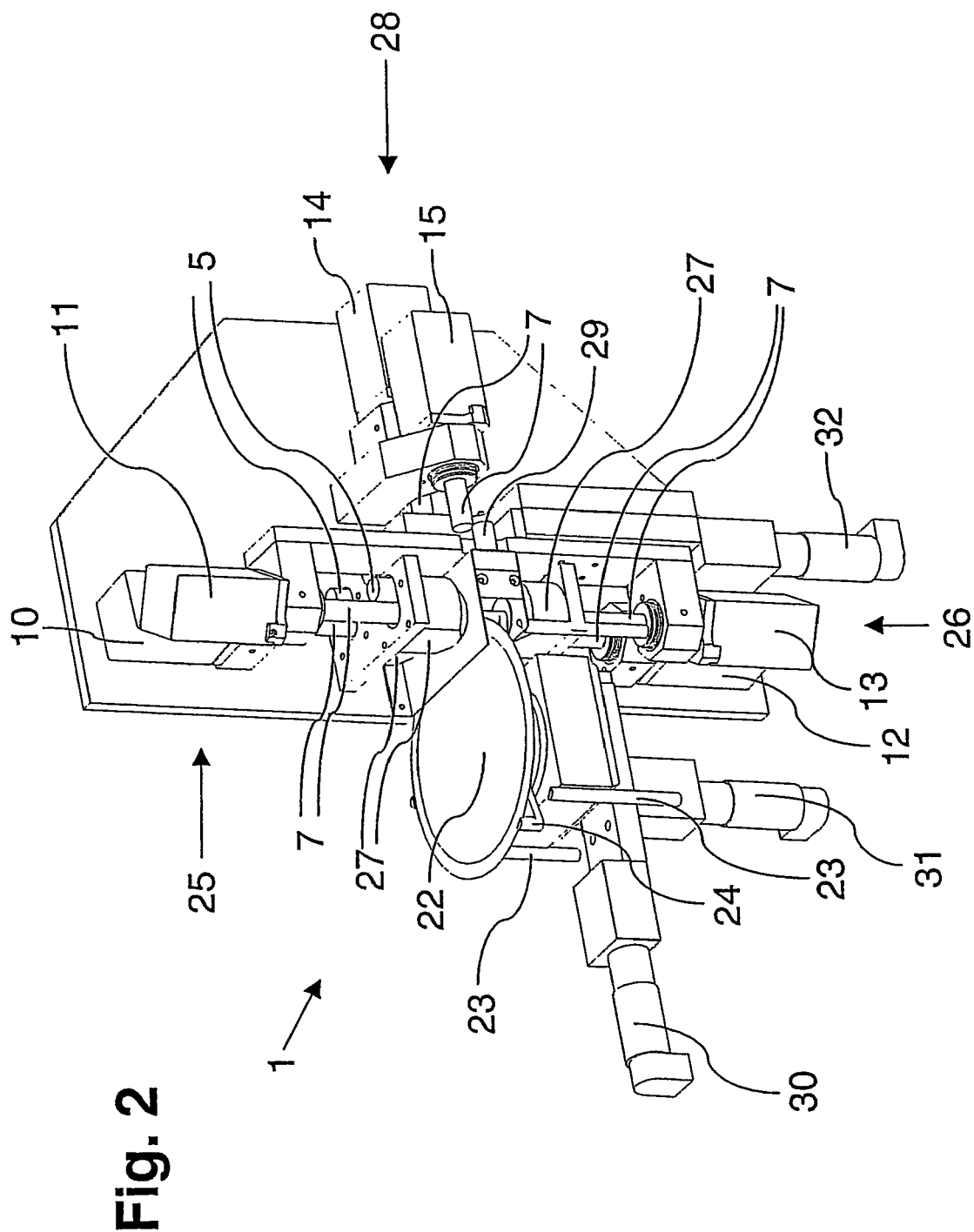
FIG. 2 is an enlarged perspective detail view of the measuring unit of the apparatus of FIG. 1.

FIG. 2 is an enlargement of a section of FIG. 1, and schematically illustrates a perspective view of a measuring unit 1 in greater detail. The object being tested is a wafer 22, whose circular peripheral edge is intended to undergo an optical quality inspection. The wafer 22 is supplied to the measuring unit 1 via a handling robot (not shown). To this end, loading pins 23 are used to receive the wafer 22 from the handling robot, or to transfer it to the handling robot after completion of the measuring operation. A chuck drive 24 provides for the rotation of the wafer 22.

A total of six camera systems 10-15 are provided, with two camera systems 10, 11 being oriented vertically from the top to the upper edge zone of the wafer 22, two camera systems 12, 13 from the bottom to the lower edge zone, as well as two camera systems 14, 15 horizontally to the lateral edge of the wafer 22. Associated to each of the camera systems 10-15 is a combined, magnifying optical imaging system 7, which permits imaging the light radiating from the wafer 22 due to reflection, refraction and/or diffraction in the respective camera system 10-15.

The six light guides 5, of which only the end pieces are shown in FIG. 2 for reasons of clarity, supply the light from the high-output cold-light sources 4. For an upper measuring head 25 with the two cameras 10 and 11, and for a lower measuring head 26 with the two cameras 12 and 13, the light received via the light guides 5 is respectively supplied to optical components 27 for generating a dark field illumination. With the use of dark field illumination, it is achieved that the nondiffracted central maximum of zeroth order does not lie in the optical axis and is thus excluded from observation. With that, it is possible and very advantageous to make visible thin, linear structures, for example, edges or scratches.

A horizontally arranged intermediate measuring head 28 with the two camera systems 14 and 15 operates with two different illuminations. In the case of the rear camera system 14, the light is likewise radiated, as aforesaid, in the sense of a dark-field illumination to the lateral edge of the wafer 22. However, for the front camera system 15, optical components 29 are provided, which are used to generate a bright-field illumination. In the case of a bright-field illumination, the light bundles for illumination and observation coincide, and the image taken by the camera system 15 appears dark in front of a light background.

To adjust the correct relative position between the wafer 22 and the individual measuring heads 25, 26, 28, diverse feed devices are provided, namely on the one hand a horizontal tracking unit 30 and a vertical tracking unit 31 for horizontally and vertically advancing the wafer 22, and on the other hand an additional vertical tracking unit 32 for vertically tracking the measuring head 28 along the edge of the wafer 22. The tracking units 30, 31, 32 can be addressed by a control and adjustment unit, which responds within shortest reaction times to changes in the relative position between the wafer 22 and the measuring heads 25, 26, 28, and which corrects the position via a corresponding regulation process.

On the evaluation computers 9, imaging software is implemented, which detects the actual position of the measuring heads 25, 26, 28 relative to the edge of the wafer 22. From the received image data of the edge region of the wafer 22, defects are detected and extracted by means of the software, and subsequently subjected to a classification. Finally, the evaluated data are processed to user needs and made available at the work station 17 for viewing on the screen 21 and for further analysis.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for optically testing the quality of objects having a peripheral edge region, comprising the steps of
    directing light onto the edge region of the object,
    detecting light radiating from the edge region of the object due to reflection, refraction or diffraction by means of at least one measuring unit, and processing the detected light in said at least one measuring unit to produce an image,
    evaluating the produced image to permit an identification of defects on or in the edge region of the object,
    monitoring spacing between the object and said at least one measuring unit, wherein an actual position of said at least one measuring unit relative to the edge region of the object is determined, and
    regulating the spacing so that it is automatically maintained substantially constant during the testing process by means of a vertical feed device or a horizontal feed device.

2. The method of claim 1, wherein the object is at least in part transparent.

3. The method of claim 1, wherein the object is a silicon wafer.

4. The method of claim 1, comprising the further step of automatically classifying the determined defects.

5. The method of claim 4, wherein the determined defects are classified by means of image processing methods.

6. The method of claim 4, wherein the determined defects are classified by means of form and intensity features over parameter ranges.

7. The method of claim 4, wherein the determined defects are classified in a catalog of defects by means of previously detected image signals.

8. The method of claim 1, wherein the evaluating step includes the step of preparing the results for display or recording.

9. The method of claim 1, wherein said at least one measuring unit is automatically tracked by a motor-operated unit horizontally or vertically as a function of the spacing that is detected between the object and the measuring unit.

10. The method of claim 1, wherein along the circumference of the object, measured values are taken at a distance of about 2 micrometers.

11. The method of claim 1, wherein in the edge region of the object measured values are taken in the direction toward the edge region at a distance of about 2 micrometers.

12. The method of claim 1, wherein in the edge region of the object, defects are detected which are of a size less than 1 micrometer.

13. The method of claim 1, wherein the object is a generally planar wafer, wherein said at least one measuring unit is spaced from the wafer in a direction generally perpendicular to the generally planar wafer, wherein the step of monitoring the spacing includes monitoring the spacing in said generally perpendicular direction, and wherein the step of regulating the spacing comprises maintaining the spacing in said generally perpendicular direction.

14. The method of claim 1, wherein the actual position of the measuring unit relative to the edge region of the object is determined from the received detected light.

15. The method of claim 1, wherein the actual position of the measuring unit relative to the edge region of the object is determined by means of an additional sensor arrangement.

16. The method of claim 15, wherein the additional sensor arrangement utilizes a capacitive measurement and/or laser triangulation.

17. An apparatus for optically testing the quality of objects having a peripheral edge region, comprising
at least one light emitting illumination unit for illuminating the edge region of the object,
at least one measuring unit configured to receive the light radiating from the edge region of the object due to reflection, refraction, or diffraction, and including an optical imaging system for producing an image from the received light,
an evaluation unit configured to receive the produced images so as to permit the identification of defects on or in the edge region of the object,
means for monitoring spacing between the object and said at least one measuring unit, wherein an actual position of said at least one measuring unit relative to the edge region of the object is determined, and
regulating means for automatically maintaining said spacing substantially constant during the testing process by means of a vertical feed device or a horizontal feed device.

18. The apparatus of claim 17, wherein the illumination unit comprises an LED, or a cold-light source, or a laser, or a conventional light source.

19. The apparatus of claim 17, wherein the illumination unit is configured to generate different luminous flux densities.

20. The apparatus of claim 17, wherein the illumination unit is mounted to permit adjustment of the angle of illumination.

21. The apparatus of claim 17, wherein the optical imaging system comprises a matrix array camera or a linear array camera.

22. The apparatus of claim 17, wherein the optical imaging system comprises at least one camera which is pivotally mounted for adjusting different angles of view of the camera.

23. The apparatus of claim 22, wherein the at least one camera is a standard linear array camera with one pixel per picture element, or a time delay integration linear array camera with a plurality of pixels per picture element.

24. The apparatus of claim 17, further comprising a motor operated unit for rotating the object.

25. The apparatus of claim 24, wherein the motor operated unit comprises loading pins for receiving the object from a robot arm and for transferring the object to the robot arm.

26. The apparatus of claim 17, further comprising an optical component which receives light from the at least one light emitting illumination unit and generates a dark field illumination therefrom.

27. The apparatus of claim 17, further comprising a loading device for supporting the object in a generally horizontal plane, and wherein the evaluation unit is positioned so as to be spaced in a generally vertical direction from said loading device, and wherein the regulating means comprises means for selectively moving said evaluation unit and said loading device relative to each other in said vertical direction.

28. The apparatus of claim 27 wherein the regulating means further comprises a closed loop automatic control.

* * * * *